United States Patent
Gedeon et al.

(10) Patent No.: US 10,080,510 B2
(45) Date of Patent: Sep. 25, 2018

(54) BREATH ANALYSING AND TRAINING ASSEMBLY

(71) Applicant: SENSEBREATH AB, Sorunda (SE)

(72) Inventors: Andras Gedeon, Stockholm (SE); Paul Krill, Jarfalla (SE)

(73) Assignee: SEEBREATH AB, Stockholm (SE)

( * ) Notice: Subject to any disclaimer, the term of this patent is extended or adjusted under 35 U.S.C. 154(b) by 267 days.

(21) Appl. No.: 14/912,830

(22) PCT Filed: Aug. 18, 2014

(86) PCT No.: PCT/SE2014/050945
§ 371 (c)(1),
(2) Date: Feb. 18, 2016

(87) PCT Pub. No.: WO2015/030648
PCT Pub. Date: Mar. 5, 2015

(65) Prior Publication Data
US 2016/0192861 A1    Jul. 7, 2016

Related U.S. Application Data

(60) Provisional application No. 61/870,858, filed on Aug. 28, 2013.

(51) Int. Cl.
*A61B 5/08* (2006.01)
*A61B 5/00* (2006.01)
(Continued)

(52) U.S. Cl.
CPC ............ *A61B 5/082* (2013.01); *A61B 5/0816* (2013.01); *A61B 5/0836* (2013.01); *A61B 5/097* (2013.01);
(Continued)

(58) Field of Classification Search
CPC .. A61B 5/08; A61B 5/00; A61B 5/097; A61B 5/6898; A61B 5/0816;
(Continued)

(56) References Cited

U.S. PATENT DOCUMENTS

| 6,929,008 B2 * | 8/2005 | Geist ............... A61M 16/08 128/202.22 |
| 2009/0095290 A1 * | 4/2009 | Cain .................. A61L 2/206 128/202.22 |

(Continued)

FOREIGN PATENT DOCUMENTS

| JP | 2004-304517 A | 10/2004 |
| JP | 2006-279744 A | 10/2006 |

OTHER PUBLICATIONS

International Search Report, dated Nov. 6, 2014, from corresponding PCT Application.
(Continued)

*Primary Examiner* — Navin Natnithithadha
*Assistant Examiner* — Eric Messersmith
(74) *Attorney, Agent, or Firm* — Young & Thompson

(57) ABSTRACT

A breath analyzing and training assembly for detecting CO2 concentration in the breathing gas of a user, includes a selective colorimetric CO2 detector having a detector surface which rapidly and reversibly changes color with CO2 concentration, when exposed thereto, and an adapter including: a docking part for receiving a mobile unit including an image capturing element, a display, and a processing element, the docking part configured to position the image capturing element in a fixed relation to the colorimetric detector, such that the image capturing element captures images of the detector surface; a detector holding part for receiving the colorimetric detector; a conduit for leading breathing gas to and from the user such that part thereof passes the detector surface; wherein the processing element (Continued)

measures CO2 concentration changes in the breathing gas by identifying color changes of images of the detector surface captured by the image capturing element.

13 Claims, 3 Drawing Sheets

(51) Int. Cl.
*A61B 5/083* (2006.01)
*G01N 33/00* (2006.01)
*G01N 33/497* (2006.01)
*A61B 5/097* (2006.01)

(52) U.S. Cl.
CPC .......... *A61B 5/6898* (2013.01); *A61B 5/7271* (2013.01); *A61B 5/742* (2013.01); *G01N 33/0008* (2013.01); *G01N 33/497* (2013.01); *A61B 5/741* (2013.01); *A61B 2560/0223* (2013.01); *A61B 2560/0456* (2013.01)

(58) Field of Classification Search
CPC ..... A61B 5/0836; A61B 5/082; A61B 5/7271; A61B 5/742; A61B 5/741; A61B 2560/0223; A61B 2560/0456; G01N 33/0008; G01N 33/497
See application file for complete search history.

(56) References Cited

U.S. PATENT DOCUMENTS

| | | | |
|---|---|---|---|
| 2010/0118179 A1* | 5/2010 | Ciudad | H04N 5/2354 348/371 |
| 2010/0310425 A1 | 12/2010 | Piper | |
| 2010/0317986 A1* | 12/2010 | Colman | A61B 5/0836 600/532 |
| 2012/0123287 A1 | 5/2012 | Gedeon | |
| 2012/0330161 A1 | 12/2012 | Kobayashi et al. | |
| 2013/0150746 A1* | 6/2013 | Tao | G06Q 50/22 600/531 |
| 2013/0259749 A1* | 10/2013 | Moretti | G01N 21/783 422/85 |
| 2015/0055134 A1* | 2/2015 | Papautsky | G01N 21/25 356/408 |
| 2015/0359458 A1* | 12/2015 | Erickson | G01N 33/52 455/557 |
| 2016/0245830 A1* | 8/2016 | Mace | A61B 5/0075 |

OTHER PUBLICATIONS

Hanna Kuutmann et al: "Smartphone Capnography—evaluation of the concept and the associated CO2 indicating sensor", May 30, 2014 (May 30, 2014), XP55147420, Stockholm, Sweden, Retrieved from the Internet: URL:http://seebreath.com/data/Master%20thesis%20smartphone%20capnography%20(ver.%2013.7).pdf [retrieved on Oct. 17, 2014].

* cited by examiner

BREATH ANALYSING AND TRAINING ASSEMBLY

FIELD OF THE INVENTION

The present invention relates to a breath analysing and training assembly for measuring exhaled carbon dioxide (CO2) concentration suitable for analysing and training the breathing of a person. More particularly, the invention relates to an assembly that is inexpensive and user-friendly and that advantageously may easily be used at home.

BACKGROUND OF THE INVENTION

Infrared absorption (IR) is the state of the art method for measuring exhaled carbon dioxide (CO2) concentration and has been in clinical use for more than 30 years. It is fast responding, selective and stable and is used routinely by monitors in the operating theatre and in postoperative care. The exhaled CO2 concentration curve (called capnograph) has also been used together with respirator treatment and for more sophisticated diagnostics for instance of lung function. Together with information about the exhaled gas flow the capnograph can be used to calculate the amount of CO2 issued from the lung and this information allows the assessment of metabolic and cardiopulmonary conditions.

The IR technology is inherently complex and bulky with advanced optical and electronic components, but in recent times compact models have been developed that are portable and can also be used in emergency situations.

A different method of detecting CO2 is based on durable, rapid and reversible colorimetric detectors that change color with the concentration of the CO2. The method is presented in A Gedeon, P Krill and C Mebius: A new colorimetric breath indicator (Colibri), Anaesthesia 1994 (49) 798.

This is inherently a less complex technology but nevertheless an opto-electric system is required to produce a signal that represents the color of the sensor surface. This technique is less accurate than the IR system and does not fully meet the requirements of a modern monitor for clinical use.

However, recently it has been shown that capnography could play an important role in the home environment for improving the quality of life of people suffering from several common diseases that are associated with disturbed breathing patterns, such as asthma and different anxiety disorders. This is discussed for instance in the following publications.

T Ritz, A E Meuret, F H Wilhem, W T Roth: Changes in pCO2, Symptoms and Lung Function of Asthma Patients During Capnometry-assisted Breathing Training. Appl Psychophysiol Biofeedback 2009 (34) 1

A E Meuret, F H Wilhem, T Ritz, W T Roth: Feedback of end-tidal pCO2 as a therapeutic approach for panic disorder. Journal of Psychiatric Research 2008 (42) 560

For home use to be feasible, the entire capnograph system must be compact, very simple to use, and at least an order of magnitude less expensive than the most inexpensive IR-based units available today. Furthermore the system must be able to continuously give feedback to the user about the results obtained and provide directions on the proper actions to be taken during breathing exercise to further improve the condition of the user. It is also a desirable feature to be able to store the results for easy transmission to an external party at a distant location.

The inventors have recognized that several important functionalities are potentially available in standard so-called smartphones. Smartphones have been suggested as means of obtaining metabolic data to help tailor nutrition therapy in various disease states, which is described in US-2013/0150746 that relates to a metabolic analyser that measures exhaled oxygen and carbon dioxide to implement a method for weight and/or fitness management. In one embodiment of the metabolic analyser a built-in camera in a cellular telephone is used to detect color changes of sensing materials when breath flow passes in order to measure the oxygen and carbon dioxide levels. Specifically, the sensing material is in the shape of an assembly of nanoparticles forming a porous membrane sensor.

The present invention addresses all the above requirements of home applications of capnography. In particular, the object of the present invention is to provide a most convenient, simple and inexpensive way to perform so called capnography-assisted breath training as for instance described in the above cited medical publications.

SUMMARY OF THE INVENTION

The above-mentioned objective is achieved by the present invention according to the independent claim.

The present invention is based upon the well-established technique of colorimetric CO2 sensing. More specifically, a thin membrane is provided with a smooth continuous coating of chemicals so that its surface changes color selectively for CO2 and in a fast, reversible way meaning that if the membrane is for instance blue in room air and yellow at about 5% CO2 then it will change from blue to yellowish during a typical exhalation and then return to the initial blue color during inspiration. It will thus cycle between blue and yellowish during breathing.

Thus, the assembly according to the invention provides for connecting a mobile unit, e.g. a standard smartphone, with an easily exchangeable colorimetric detector. An adapter is provided such that it can keep the smartphone in place and at the same time hold the colorimetric detector surface at a fixed suitable position relative to the image capturing means (e.g. camera) of the mobile unit (e.g. smartphone). The adapter also shields the detector surface from uncontrolled external illumination and ambient air and provides a conduit for the breathing gas flowing to and from the patient so that at least some part of this gas passes over the sensing surface.

An application program is further provided which is executed by the mobile unit enabling an interactive use of the assembly. The mobile unit may provide audible user instructions, e.g. instructing the user when to breath during a measurement session. Furthermore, the result of the measurements may be presented on the smartphone's display.

SHORT DESCRIPTION OF THE APPENDED DRAWINGS

DETAILED DESCRIPTION OF PREFERRED EMBODIMENTS OF THE INVENTION

Figure 1:
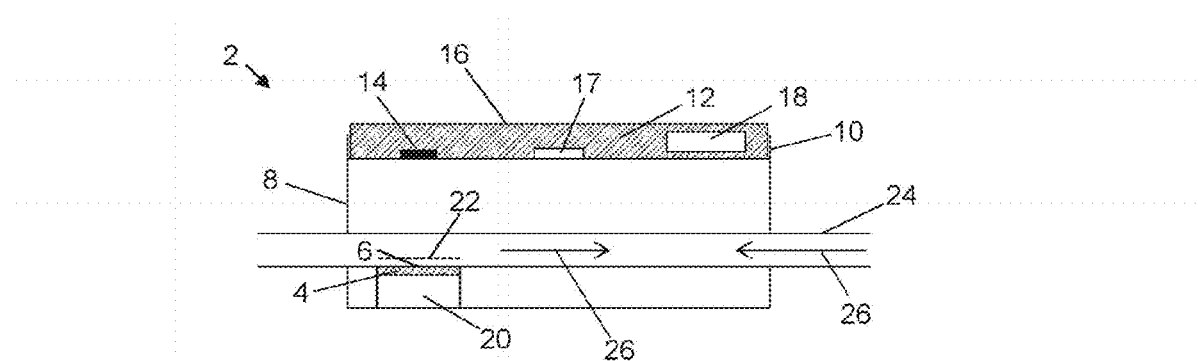
FIG. 1 is a schematic cross-sectional view of the assembly.

First with references to FIG. 1 the present invention will now be described in detail. Thus, the present invention relates to a breath analysing and training assembly 2 adapted to sense the carbon dioxide (CO2) concentration in the breathing gas of a user. The assembly 2 comprises a selective colorimetric CO2 detector 4 provided with a detector surface 6 adapted to change color rapidly and reversibly with the concentration of CO2, when exposed to CO2, and an adapter 8.

The adapter 8 comprises:
- A docking part 10 for receiving a mobile unit 12 comprising an image capturing means 14, and a processing means 18. Advantageously the assembly 2 comprises a display 16, e.g. arranged on said mobile unit. The mobile unit may be received and attached and then released when the measurement session have been concluded. The docking part 10 is configured to position the image capturing means 14 in a fixed relation to the colorimetric detector 4, such that the image capturing means 14 is adapted to capture images of said detector surface 6.
- A detector holding part 20 adapted to receive the colorimetric detector 4 and attach the detector. In addition the detector holding part 20 enables that the detector easily may be exchanged. The adaptor 8 or the detector holding part 20 preferably includes a detector surface protecting means 22 adapted to protect the surface 6 from ambient air in an airtight fashion when no measurement is performed.
- A breathing conduit 24 to lead breathing gas to and from said user such that at least a part of the breathing gas passes the detector surface.

The processing means is to be interpreted broadly as one or many circuits provided with advanced processing capacity, large storage capacity, communication capabilities, etc. E.g. having some or all capabilities of so-called smartphones.

The processing means 18 is adapted to execute an application program to perform a measurement session including a measurement step that includes measuring CO2 concentration changes in breathing gas by identifying color changes of images of the detector surface 6 captured by said image capturing means 14.

Figure 4:
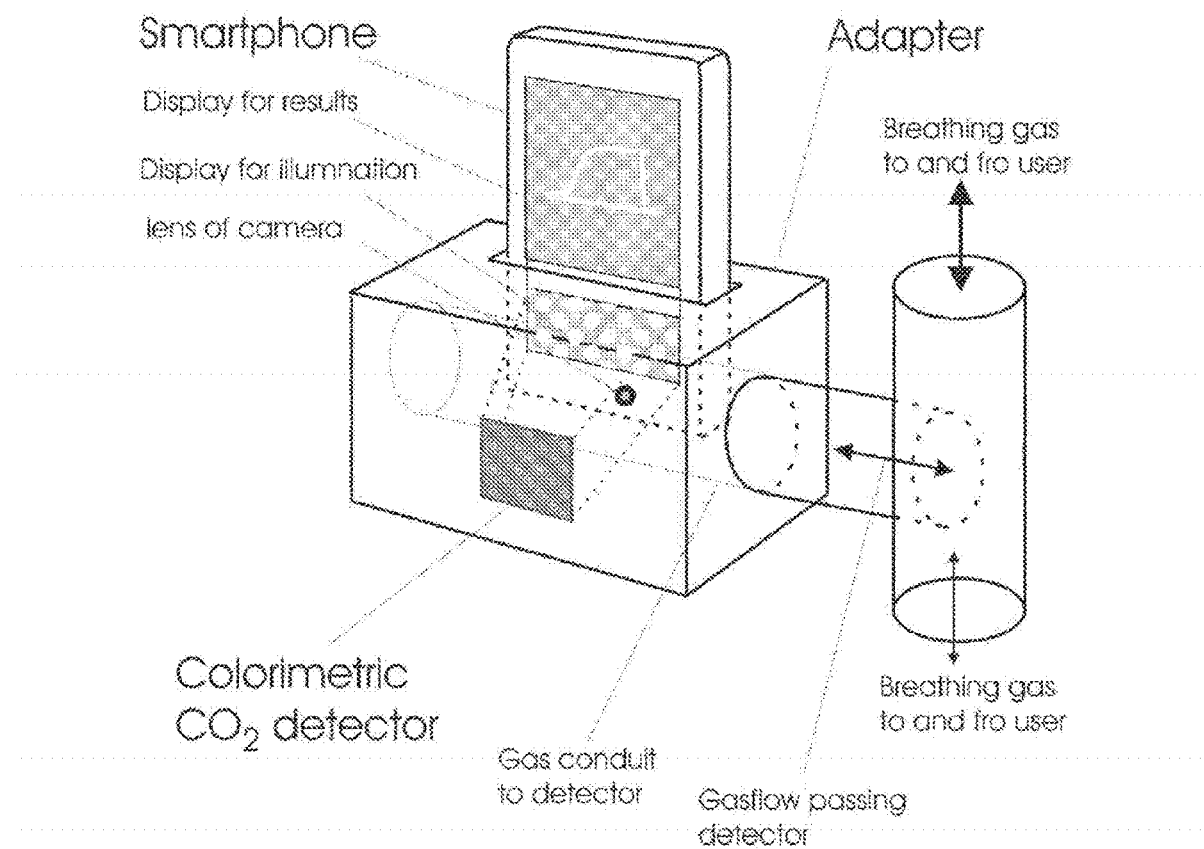
FIG. 4 is a perspective view of one embodiment of the assembly.

The docking part 10 has a shape that essentially corresponds to relevant parts of the mobile unit, e.g. being an opening in the enclosure shell of the adapter that is shaped as the cross-section of the mobile unit, see e.g. FIG. 4. The mobile unit is preferably held in place by a frictional fit but specific attachment means may naturally also be arranged, e.g. in the form of straps, etc.

The breathing conduit is preferably embodied as a tube. Close to the adapter the tube is essentially rigid but is made more flexible at the end were the mouthpiece into which the user breathes is arranged.

Advantageously, the detector surface protecting means 22 is adapted to be moved to a non-protection position, such that said detector surface is available for measurements. This is important, both with regard that the detector surface 6 is made available for image capturing and that the detector surface may be reached by the breathing gas.

And more advantageously, the detector surface protecting means 22 is adapted to be automatically moved to a non-protection position when the mobile unit is received by the docking part, such that said detector surface is available for measurements.

The detector surface protecting means may have the shape of a hinged lid that is automatically forced to the non-protection position by a link arrangement. The link arrangement may also be manually activated by means of a simple button or lever at the outside of the adapter. The lid may be spring-actuated such that it is forced back to be in the protection position when no measurement is performed.

In a preferred embodiment the mobile unit is a smartphone. This embodiment is illustrated by the schematic perspective view in FIG. 4.

The mobile unit may also be embodied by so called smartcameras, tablet computers or any other device with similar capabilities.

In one embodiment the image capturing means is a camera unit, e.g. of the type normally available in smartphones.

The assembly also comprises an illumination means 17 adapted to illuminate the detector surface during measurement. According to one embodiment the illumination means is embodied by at least a part of the display.

It should be noted that the light source 17 used to illuminate the detector surface may emit white light or light with one or more distinct colors that can be advantageously chosen to optimize the accuracy and repeatability of the measurements. The light source may be a part of the mobile unit (e.g. smartphone) such as the lamp for the flash or the actual display of the smartphone. This latter arrangement is shown in FIG. 4.

However, the adapter can also be fitted with a simple battery operated illumination means (for instance using standard white LED illumination or LED-s with one or more distinct colors) that could be activated manually or automatically when the smartphone is attached. In this way an external illumination of the sensor surface is achieved that saves the battery time of the phone.

During one measurement step a predetermined number of successive images are taken, preferably at least 4-5 images per second, or a video is produced, by the image capturing means, e.g. the camera unit of the mobile unit (smartphone) of at least a part of the detector surface, and wherein said measurement step has a predetermined duration to record at least one breath, preferably in the range of 0.1-15 seconds.

The processing means is then adapted to calculate capnographs based upon the captured image information and preferably display the calculated capnographs and/or the etCO2 value (the last CO2 concentration value before inhalation starts).

In order to interpret the captured image information the processing means is adapted to use at least one characteristic optical property of the detector surface, such as the color, or the reflectance. The characteristic optical property is stored in the processing means. In addition the processing means is adapted to store at least one relationship between the characteristic optical property of the detector surface and the corresponding concentrations of CO2.

Figure 2:
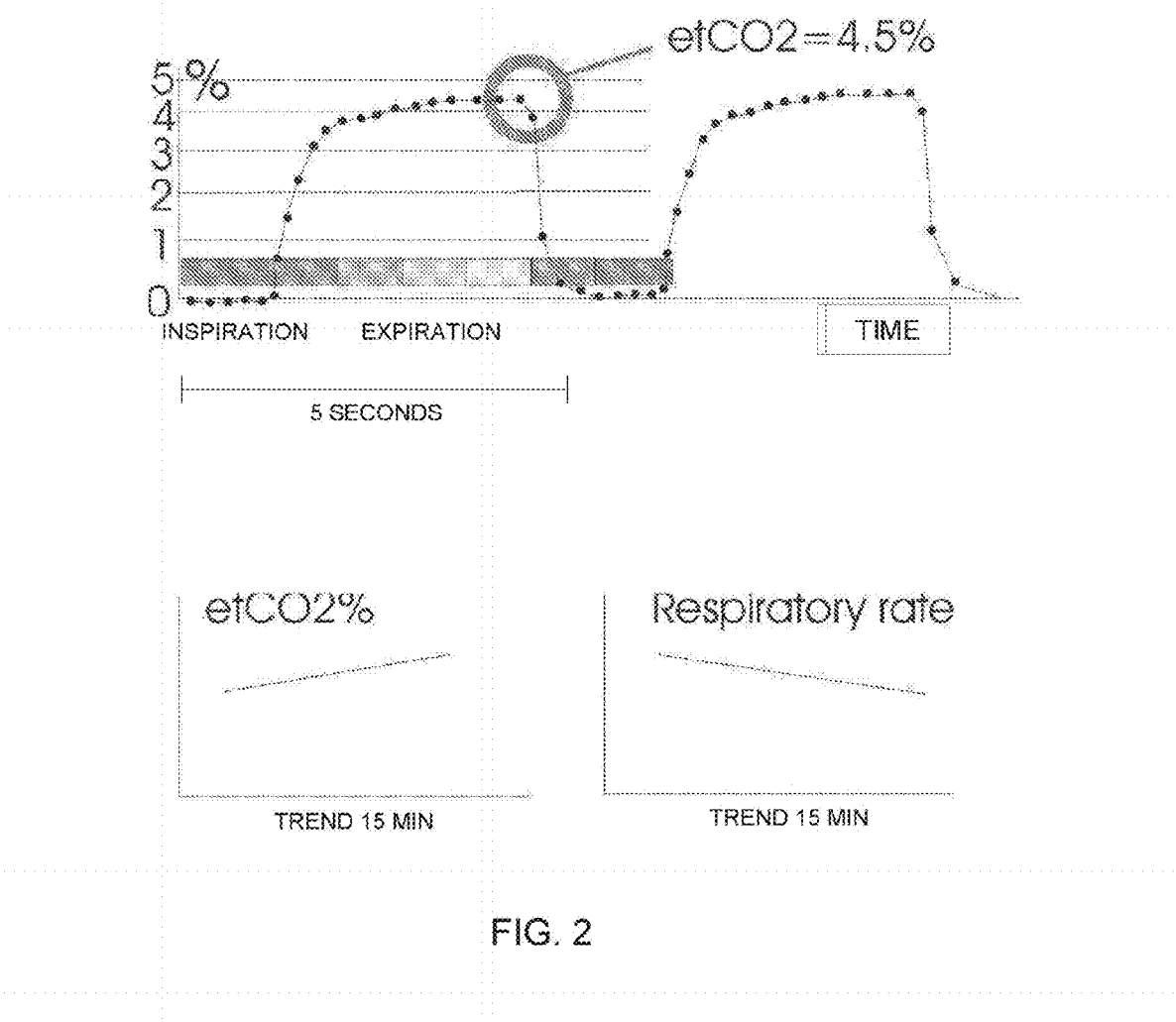
FIG. 2 illustrates different exemplary graphs.

For each image or selected frame from the video, the processing means encodes the color (or any other specific characteristic optical property) and then compares this to a reference color scale that translates the encoded color (or characteristics) into a CO2 concentration percentage. How the preprinted reference color scale translates into CO2 concentration is established at the factory for the colorimetric detector e.g. by using calibrated CO2 gas concentrations. The concentration obtained in this way for each image corresponds to a certain point in time, namely when the image is taken, and the images together therefore trace out a capnograph. This is illustrated in FIG. 2 by the graph at the top. Values from specific images are illustrated by dots. The inspiration part and the expiration part of the curve are denoted as well as the end tidal CO2 concentration (etCO2) which in this case is 4.5%.

There are several alternative ways to establish the color reference scale needed to convert a color surface image to concentration. The simplest method is to determine a set of colors—as an example 30 shades between blue and yellow—that corresponds to concentration steps of 0.2% $CO_2$—from 0 to 5.8% (in color scale from blue to yellow).

Figure 3A:
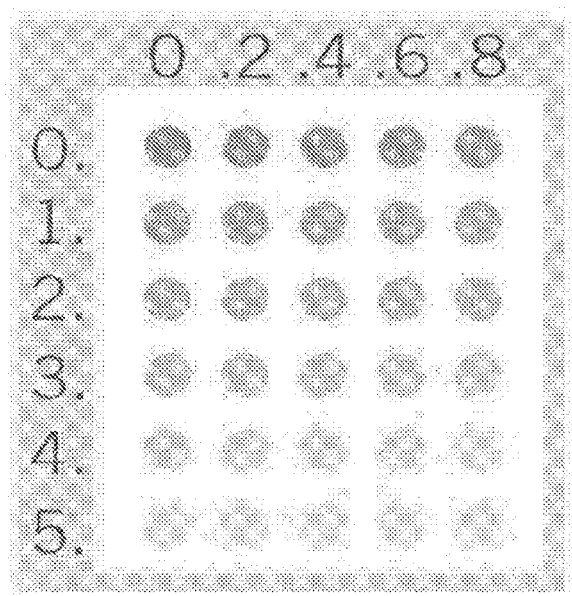
FIGS. 3a and 3b illustrate different color reference scales and their uses.

This is shown in FIG. 3a, in a grey scale, where the vertical column denotes the percentage value and the horizontal column denotes the decimal percentage value. The color of the sensor surface image is compared to these predetermined color steps to find the best match and so the $CO_2$ concentration at hand.

Figure 3B:
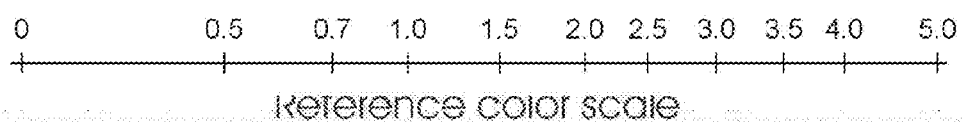
Figure 3B:
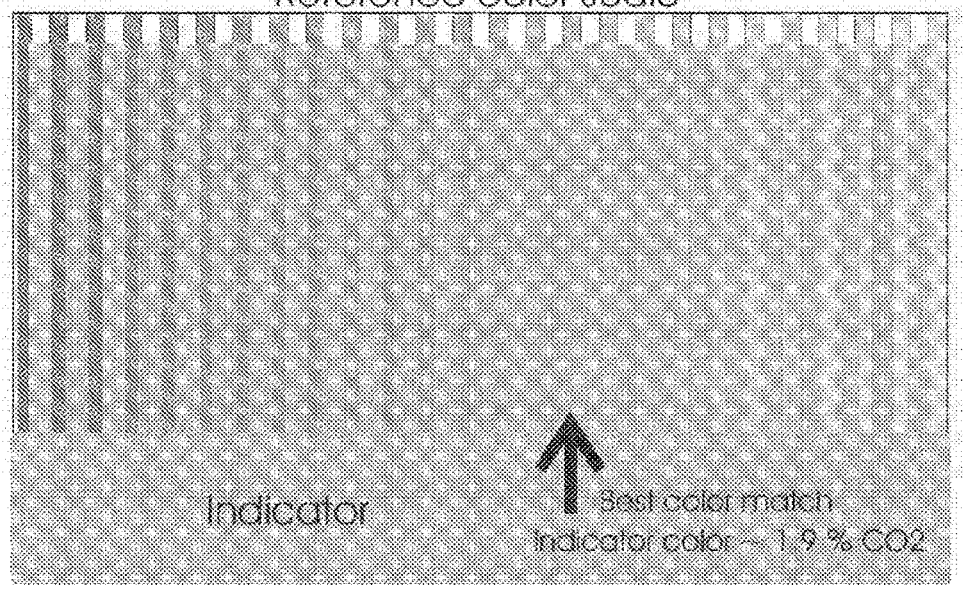

Another method is to print a reference color scale next to the indicating sensor surface and allow the camera to always include the reference scale with the indicating surface in the same image. A comparison is then made in each image to find the best correspondence between the color of the detector and the printed reference scale, thereby determining the $CO_2$ concentration in question. FIG. 3b shows what happens if a series of color stripes representing the reference scale is placed on top of the indicator. The camera image at any time shows where the color of the indicator matches the color scale best—and the processing means determines the corresponding $CO_2$ concentration—which in the case shown is ~1.9%.

A third alternative involves enclosing the detector surface in an atmosphere of a certain known $CO_2$ concentration when packaged and sealed from the ambient before storage. This sealing is made of materiel transparent to light and can be manually easily removed. On mounting the detector into the adapter the image capturing means, e.g. the camera, will image the color of the sealed detector surface and calibrate the unit at the chosen concentration. After this the user removes the seal and the detector surface turns to the color of the ambient, for example blue, since the ambient air contains negligible amount of $CO_2$. In this way the zero concentration color of the detector surface can also be used to calibrate the assembly. Then the remaining values are calculated from a known color/concentration relationship that connects the two calibration points.

Comparison to a reference at the start of use allows for a determination of the status of the detector. A small deviation from the color expected for zero concentration due to the deterioration of the detector with time can be compensated for by adjusting the reference scale in a predetermined manner while a larger deviation can result in a recommendation to replace the detector.

Thus, according to one embodiment the measurement session includes checking of the detector quality. This detector quality check may be performed by simultaneously comparing different parts of images of the detector surface, where these different parts preferably are chosen such that one part is close to the centre of the detector surface, i.e. at a distance from the detector surface edge, and the other part is close to the detector surface edge, which more likely will deteriorate faster. If these different parts exhibit different performance an indication is given that it is time to exchange the detector. Alternatively, the differences may result in a correction to the concentration calculation. The detector quality check may also be performed at start of a measuring session by comparison of the optical properties of the detector surface to a reference value when $CO_2$ is absent. The result may guide the choice of the color of illumination, lead to a correction to the concentration calculation or again a replacement of the detector.

In addition to determining the $CO_2$ concentration the processing means preferably is adapted to calculate and display end tidal $CO_2$ (et $CO_2$) concentration values and/or respiratory rates at the display.

Furthermore, the processing means may calculate and display average values and/or trends of predetermined parameters related to the capnographs, end tidal $CO_2$ (et$CO_2$) values and/or respiratory rates. This is illustrated by the graphs at the bottom of FIG. 2, whereas the et$CO_2$ trend (to the left) and the respiratory rate trend (to the right) during 15 minutes are respectively indicated.

The mobile unit preferably includes an audio unit and wherein auditory instructions may be generated to direct and guide the user during a measurement session via the audio unit, e.g. in response to the results obtained, or in order to provide training instructions to the user.

The application program is executed by the mobile unit enabling an interactive use of the assembly. The mobile unit may provide audible user training instructions, e.g. instructing the user when to breath during a measurement session. The user training instructions may e.g. be of the kind described in articles cited in the background section for use by asthma patients or patients with anxiety disorders.

The mobile unit, e.g. the smartphone, is inherently suited to store the data and provided with communication capabilities to send information directly or on demand to outside parties for evaluation. The results may be communicated using wireless, IR, Bluetooth or cable wise.

With regard to the $CO_2$ detector it preferably comprises a porous material containing in its pores a phase transfer agent and a pH sensitive color indicator. Advantageously, the phase transfer agent is tetraoctyammoniumhydroxide and the pH sensitive color indicator is thymol blue.

US-2012/0123287 relates to a portable device for breathing detection that includes a colorimetric $CO_2$ detector which is advantageously used in connection with the present invention. This patent application is assigned to the present assignee and is incorporated by reference herein in its entirety.

The porous material may be e.g. a porous polymeric material such as known to the person skilled in the art, which material should be capable of absorbing or otherwise binding the phase transfer agent and pH sensitive color indicator. In some embodiments, the porous material is a membrane filter, such as a polyethersulfone membrane. However, other porous materials may also be used, e.g. acetylated cellulose layer on a polyester film.

There are a number of pH sensitive dies available to the skilled person, and particular examples are given e.g. in the prior art document referred to herein above. In one embodiment, the indicator comprises one or several dies selected from thymol blue, cresol red and cresol purple.

The phase transfer agent(s) may comprise at least one water insoluble organic quarternary (e.g. ammonium or phosphonium) hydroxide, e.g. tetraoctyl ammonium hydroxide.

For example, the $CO_2$ detector may comprise a porous material containing in its pores tetraoctylammoniumhydroxide as a phase transfer agent and thymol blue as a pH sensitive color indicator.

EXAMPLE

A typical application program may interface with the user the following steps:

Activate the application (user action).

"Place smartphone in adapter" (application instruction; audible or via display).

"When you are ready, press start at the display" (application instruction; audible or via display).

When start is pressed and the assembly is ready for detection; a measurement time window opens and the assembly awaits that the user breaths.

Detection of $CO_2$ concentration.

Repeat breathing in line with the instructions given audible or via display

End of measurement.

Result, e.g. $etCO_2$ trend, is presented on the display.

Recommendation/comment for a follow-up session is given via display and/or audible The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A breath analysing and training assembly adapted to detect the carbon dioxide ($CO_2$) concentration in the breathing gas of a user, and a mobile unit comprising an image capturing means, a display and a processing means, the assembly comprises a selective colorimetric $CO_2$ detector provided with a detector surface adapted to change color rapidly and reversibly with the concentration of $CO_2$, when exposed to $CO_2$, and an adapter comprising a docking part for receiving and attaching said mobile unit, wherein the docking part is configured to position said image capturing means in a fixed relation to said colorimetric detector, such that said image capturing means is adapted to capture images of said detector surface, wherein at least a part of said display is arranged to illuminate said detector surface during image capturing, a detector holding part adapted to receive said colorimetric detector and attach said detector, a breathing conduit to lead breathing gas to and from said user such that at least a part of the breathing gas passes the detector surface, and a detector surface protecting means adapted to protect the surface from ambient air in an airtight fashion when no measurement is performed, the detector surface protecting means being movable from a protection position to a non-protection position when said mobile unit is received by said docking part, said detector surface being available for measurements, when said detector surface protecting means is in said non-protection position, and wherein said processing means is adapted to execute an application program adapted to perform a measurement session including a measurement step that includes measuring $CO_2$ concentration changes in breathing gas by identifying changes in the optical characteristics of said detector surface captured by said image capturing means.

2. The assembly and mobile unit according to claim 1, wherein said mobile unit is a smartphone.

3. The assembly and mobile unit according to claim 1, wherein said image capturing means is a camera unit.

4. A breath analysing and training assembly adapted to detect the carbon dioxide ($CO_2$) concentration in the breathing gas of a user, and a mobile unit comprising an image capturing means, a display and a processing means, the assembly comprises a selective colorimetric $CO_2$ detector provided with a detector surface adapted to change color rapidly and reversibly with the concentration of $CO_2$, when exposed to $CO_2$, and an adapter comprising a docking part for receiving and attaching said mobile unit, wherein the docking part is configured to position said image capturing means in a fixed relation to said colorimetric detector, such that said image capturing means is adapted to capture images of said detector surface, wherein at least a part of said display is arranged to illuminate said detector surface during image capturing, a detector holding part adapted to receive said colorimetric detector and attach said detector, and a breathing conduit to lead breathing gas to and from said user such that at least a part of the breathing gas passes the detector surface, wherein during a measurement step a predetermined number of successive images are taken by said image capturing means of at least a part of said detector surface, and wherein said measurement step has a predetermined duration in the range of 0.1-15 seconds.

5. The assembly and mobile unit according to claim 1, wherein said processing means is adapted to store at least one characteristic optical property of the detector surface.

6. The assembly and mobile unit according to claim 5, wherein said processing means is adapted to store at least one relationship between said characteristic optical property of the detector surface and the corresponding concentrations of $CO_2$.

7. The assembly and mobile unit according to claim 1, wherein said mobile unit includes an audio unit.

8. A breath analysing and training assembly adapted to detect the carbon dioxide ($CO_2$) concentration in the breathing gas of a user, and a mobile unit comprising an image capturing means, a display and a processing means, the assembly comprises a selective colorimetric $CO_2$ detector provided with a detector surface adapted to change color rapidly and reversibly with the concentration of $CO_2$, when exposed to $CO_2$, and an adapter comprising a docking part for receiving and attaching said mobile unit, wherein the docking part is configured to position said image capturing means in a fixed relation to said colorimetric detector, such that said image capturing means is adapted to capture images of said detector surface, wherein at least a part of said display is arranged to illuminate said detector surface during image capturing, a detector holding part adapted to receive said colorimetric detector and attach said detector, and a breathing conduit to lead breathing gas to and from said user such that at least a part of the breathing gas passes the detector surface, wherein a measurement session includes a checking of detector quality by simultaneously comparing different parts of images of the detector surface.

9. The assembly and mobile unit according to claim 1, wherein a measurement session includes a checking of detector quality by a comparison of the optical characteristics of the detector to a reference in the absence of $CO_2$.

10. The assembly and mobile unit according to claim 1, wherein said CO2 detector comprises a porous material containing in its pores a phase transfer agent and a pH sensitive color indicator.

11. The assembly and mobile unit according to claim 10, wherein the phase transfer agent is tetraoctyammonium hydroxide and the pH sensitive color indicator is thymol blue.

12. The assembly and mobile unit according to claim 4, wherein during the measurement step, the predetermined number of successive images are taken at least 4-5 images per second.

13. The assembly and mobile unit according to claim 5, wherein the at least one characteristic optical property of the detector surface is one of color and reflectance.

* * * * *